United States Patent
Eckhardt et al.

(10) Patent No.: US 7,217,711 B2
(45) Date of Patent: *May 15, 2007

(54) PIPERAZIN-1-YL AND 2-([1,4]DIAZEPAN-1-YL)-IMIDAZO[4,5-D]-PYRIDAZIN-4-ONES, THE PREPARATION THEREOF AND THEIR USE AS PHARMACEUTICAL COMPOSITIONS

(75) Inventors: Matthias Eckhardt, Biberach (DE); Norbert Hauel, Schemmerhofen (DE); Frank Himmelsbach, Mittebiberach (DE); Iris Kauffmann-Hefner, Attenweiler (DE); Elke Langkopf, Warthausen (DE); Mohammad Tadayyon, Ulm (DE); Leo Thomas, Biberach (DE)

(73) Assignee: Boehringer Ingelheim International GmbH (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/016,176

(22) Filed: Dec. 17, 2004

(65) Prior Publication Data

US 2005/0171093 A1   Aug. 4, 2005

Related U.S. Application Data

(60) Provisional application No. 60/538,555, filed on Jan. 23, 2004.

(30) Foreign Application Priority Data

Dec. 17, 2003  (DE) ................. 103 59 098

(51) Int. Cl.
*C07D 487/04* (2006.01)
*A61K 31/5025* (2006.01)
*A61P 3/10* (2006.01)

(52) U.S. Cl. ................. 514/234.5; 540/575; 544/118; 544/236; 514/218; 514/248

(58) Field of Classification Search ............... 544/118, 544/236; 540/575; 514/218, 234.5, 248
See application file for complete search history.

(56) References Cited

U.S. PATENT DOCUMENTS

| 2004/0034014 A1 | 2/2004 | Kanstrup et al. |
| 2004/0116328 A1 | 6/2004 | Yoshikawa et al. |
| 2005/0020574 A1 | 1/2005 | Hauel et al. |

FOREIGN PATENT DOCUMENTS

| WO | WO 02/02560 A2 | 1/2002 |
| WO | WO 03/104229 A1 | 12/2003 |
| WO | WO 2004/050658 A1 | 6/2004 |

*Primary Examiner*—Kahsay Habte
(74) *Attorney, Agent, or Firm*—Michael P. Morris; Mary-Ellen Devlin; Thomas C. Blankinship

(57) ABSTRACT

The present invention relates to substituted imidazo[4,5-d] pyridazin-4-ones of general formula

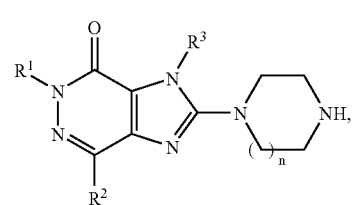

(I)

wherein $R^1$ to $R^3$ and n are defined as in claims 1 to 8, the tautomers, enantiomers, diastereomers, mixtures thereof and the salts thereof which have valuable pharmacological properties, particularly an inhibiting effect on the activity of the enzyme dipeptidylpeptidase-IV (DPP-IV).

14 Claims, No Drawings

PIPERAZIN-1-YL AND 2-([1,4]DIAZEPAN-1-YL)-IMIDAZO[4,5-D]-PYRIDAZIN-4-ONES, THE PREPARATION THEREOF AND THEIR USE AS PHARMACEUTICAL COMPOSITIONS

RELATED APPLICATIONS

Benefit of U.S. Provisional Application Ser. No. 60/538,555, filed on Jan. 23, 2004, is hereby claimed.

DETAILED DESCRIPTION OF THE INVENTION

The present invention relates to new substituted imidazo[4,5-d]pyridazin-4-ones of general formula

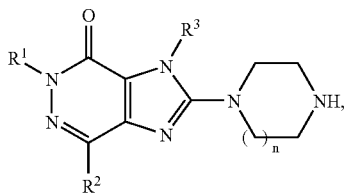

the tautomers, the enantiomers, the stereoisomers, the mixtures thereof and the salts thereof, particularly the physiologically acceptable salts thereof with inorganic or organic acids which have valuable pharmacological properties, particularly an inhibiting effect on the activity of the enzyme dipeptidylpeptidase-IV (DPP-IV), the preparation thereof, the use thereof for preventing or treating illnesses or conditions connected with an increased DPP-IV activity or capable of being prevented or alleviated by reducing the DPP-IV activity, particularly type I or type II diabetes mellitus, the pharmaceutical compositions containing a compound of general formula (I) or a physiologically acceptable salt thereof and processes for the preparation thereof.

In the above formula I $R^1$ denotes a heteroaryl-$C_{1-3}$-alkyl group,
  where the term heteroaryl denotes a pyridinyl, pyrimidinyl, phenylpyridinyl, phenylpyrimidinyl, benzoxazolyl, 1-methyl-1H-benzotriazolyl, benzo[1,2,5]thiadiazolyl, [1,2,4]triazolo[4,3-a]pyridinyl, quinolinyl, isoquinolinyl, quinazolinyl, quinoxalinyl, naphthyridinyl or phenanthridinyl group and the above-mentioned heteroaryl groups are substituted by $R^{10}$, $R^{11}$ and $R^{12}$,
    where $R^{10}$ denotes a hydrogen atom, a fluorine, chlorine or bromine atom or a methyl, difluoromethyl, trifluoromethyl, phenyl, cyano, methoxy, difluoromethoxy, trifluoromethoxy, amino, methylamino, dimethylamino, pyrrolidin-1-yl, piperidin-1-yl or morpholin-4-yl group,
    $R^{11}$ denotes a hydrogen atom or a methyl, methoxy or cyano group and
    $R^{12}$ denotes a hydrogen atom or a methyl group, or a naphthyl-$C_{1-3}$-alkyl group wherein the naphthyl moiety is substituted by $R^{13}$ and $R^{14}$,
  while $R^{13}$ denotes a hydrogen atom, a fluorine, chlorine or bromine atom or a methyl, difluoromethyl, trifluoromethyl, cyano, methoxy, difluoromethoxy or trifluoromethoxy group and $R^{14}$ denotes a hydrogen atom or a methyl, methoxy or cyano group, $R^2$ denotes a hydrogen atom or a methyl group, $R^3$ denotes a 2-butyn-1-yl group or a 1-buten-1-yl, 2-buten-1-yl- or 3-methyl-2-buten-1-yl group, and n denotes the number 1 or 2, with the exception of the compounds
2-(piperazin-1-yl)-3-(butyn-1-yl)-5-[(pyridin-2-yl)methyl]-3,5-dihydro-imidazo[4,5-d]pyridazin-4-one,
2-(piperazin-1-yl)-3-(butyn-1-yl)-5-[(pyridin-3-yl)methyl]-3,5-dihydro-imidazo[4,5-d]pyridazin-4-one,
2-(piperazin-1-yl)-3-(butyn-1-yl)-5-[(pyridin-4-yl)methyl]-3,5-dihydro-imidazo[4,5-d]pyridazin-4-one,
2-(piperazin-1-yl)-3-(butyn-1-yl)-5-[(2-methoxy-pyridin-3-yl)methyl]-3,5-dihydro-imidazo[4,5-d]pyridazin-4-one,
2-(piperazin-1-yl)-3-(butyn-1-yl)-5-[(6-amino-pyridin-3-yl)methyl]-3,5-dihydro-imidazo[4,5-d]pyridazin-4-one,
2-(piperazin-1-yl)-3-(butyn-1-yl)-5-[(5-amino-pyridin-2-yl)methyl]-3,5-dihydro-imidazo[4,5-d]pyridazin-4-one,
2-(piperazin-1-yl)-3-(butyn-1-yl)-5-[(2-fluoro-pyridin-3-yl)methyl]-3,5-dihydro-imidazo[4,5-d]pyridazin-4-one,
2-(piperazin-1-yl)-3-(butyn-1-yl)-5-[(2-fluoro-pyridin-4-yl)methyl]-3,5-dihydro-imidazo[4,5-d]pyridazin-4-one,
2-(piperazin-1-yl)-3-(butyn-1-yl)-5-[(6-fluoro-pyridin-2-yl)methyl]-3,5-dihydro-imidazo[4,5-d]pyridazin-4-one and
2-(piperazin-1-yl)-3-(butyn-1-yl)-5-[(isoquinolin-1-yl)methyl]-3,5-dihydro-imidazo[4,5-d]pyridazin-4-one, the tautomers, the enantiomers, the diastereomers, the mixtures thereof and the salts thereof.

Preferred compounds of general formula I are those wherein $R^1$ denotes a heteroarylmethyl group,
  where the term heteroaryl denotes a pyridinyl, pyrimidinyl, benzoxazolyl, 1-methyl-1H-benzotriazolyl, benzo[1,2,5]thiadiazolyl, [1,2,4]-triazolo[4,3-a]pyridinyl, quinolinyl, isoquinolinyl, quinazolinyl, quinoxalinyl, naphthyridinyl or phenanthridinyl group and the above-mentioned heteroaryl groups are substituted by $R^{10}$, $R^{11}$ and $R^{12}$,
    where $R^{10}$ denotes a hydrogen atom or a fluorine atom or a methyl, difluoromethyl, trifluoromethyl, phenyl, cyano, methoxy, difluoromethoxy, trifluoromethoxy, dimethylamino, pyrrolidin-1-yl, piperidin-1-yl or morpholin-4-yl group,
    $R^{11}$ denotes a hydrogen atom or a methyl or cyano group and
    $R^{12}$ denotes a hydrogen atom or a methyl group, or a naphthylmethyl group wherein the naphthyl moiety is substituted by $R^{13}$ and $R^{14}$,
  where $R^{13}$ denotes a hydrogen atom, a fluorine, chlorine or bromine atom or a methyl, difluoromethyl, trifluoromethyl, cyano, methoxy, difluoromethoxy or trifluoromethoxy group and
  $R^{14}$ denotes a hydrogen atom or a cyano group, $R^2$ denotes a hydrogen atom or a methyl group, $R^3$ denotes a 2-butyn-1-yl group or a 1-buten-1-yl, 2-buten-1-yl or 3-methyl-2-buten-1-yl group, and n denotes the number 1 or 2, with the exception of the compounds
2-(piperazin-1-yl)-3-(butyn-1-yl)-5-[(pyridin-2-yl)methyl]-3,5-dihydro-imidazo[4,5-d]pyridazin-4-one, 2-(piperazin-1-yl)-3-(butyn-1-yl)-5-[(pyridin-3-yl)methyl]-3,5-dihydro-imidazo[4,5-d]pyridazin-4-one,
2-(piperazin-1-yl)-3-(butyn-1-yl)-5-[(pyridin-4-yl)methyl]-3,5-dihydro-imidazo[4,5-d]pyridazin-4-one,
2-(piperazin-1-yl)-3-(butyn-1-yl)-5-[(2-methoxy-pyridin-3-yl)methyl]-3,5-dihydro-imidazo[4,5-d]pyridazin-4-one,
2-(piperazin-1-yl)-3-(butyn-1-yl)-5-[(2-fluoro-pyridin-3-yl)methyl]-3,5-dihydro-imidazo[4,5-d]pyridazin-4-one,
2-(piperazin-1-yl)-3-(butyn-1-yl)-5-[(2-fluoro-pyridin-4-yl)methyl]-3,5-dihydro-imidazo[4,5-d]pyridazin-4-one,
2-(piperazin-1-yl)-3-(butyn-1-yl)-5-[(6-fluoro-pyridin-2-yl)methyl]-3,5-dihydro-imidazo[4,5-d]pyridazin-4-one and
2-(piperazin-1-yl)-3-(butyn-1-yl)-5-[(isoquinolin-1-yl)methyl]-3,5-dihydro-imidazo[4,5-d]pyridazin-4-one, the tautomers, the mixtures and salts thereof.

Preferred sub-groups in each case are those compounds of general formula I wherein $R^1$, $R^2$ and n are as hereinbefore defined and $R^3$ denotes a 2-butyn-1-yl group, the tautomers, enantiomers, diastereomers, mixtures thereof and the salts thereof.

Particularly preferred are those compounds of general formula I wherein $R^1$ denotes a heteroarylmethyl group,
  wherein the term heteroaryl denotes a pyridinyl, pyrimidinyl, benzoxazolyl, 1-methyl-1H-benzotriazolyl, benzo[1,2,5]thiadiazolyl, [1,2,4]-triazolo[4,3-a]pyridinyl, quinolinyl, isoquinolinyl, quinazolinyl, quinoxalinyl, naphthyridinyl- or phenanthridinyl group and the above-mentioned heteroaryl groups are substituted by $R^{10}$, $R^{11}$ and $R^{12}$,
    where $R^{10}$ denotes a hydrogen atom or a fluorine atom or a methyl, phenyl, cyano, methoxy, dimethylamino, pyrrolidin-1-yl, piperidin-1-yl or morpholin-4-yl group,
    $R^{11}$ denotes a hydrogen atom or a methyl or cyano group and
    $R^{12}$ denotes a hydrogen atom or a methyl group, or a naphthylmethyl group wherein the naphthyl moiety is substituted by $R^{13}$ and $R^{14}$,
  while $R^{13}$ denotes a hydrogen atom, a fluorine or bromine atom or a cyano or methoxy group and
  $R^{14}$ denotes a hydrogen atom or a cyano group, $R^2$ denotes a hydrogen atom, $R^3$ denotes a 2-butyn-1-yl group and n denotes the number 1 or 2, with the exception of the compounds
2-(piperazin-1-yl)-3-(butyn-1-yl)-5-[(pyridin-2-yl)methyl]-3,5-dihydro-imidazo[4,5-d]pyridazin-4-one,
2-(piperazin-1-yl)-3-(butyn-1-yl)-5-[(pyridin-3-yl)methyl]-3,5-dihydro-imidazo[4,5-d]pyridazin-4-one,
2-(piperazin-1-yl)-3-(butyn-1-yl)-5-[(pyridin-4-yl)methyl]-3,5-dihydro-imidazo[4,5-d]pyridazin-4-one,
2-(piperazin-1-yl)-3-(butyn-1-yl)-5-[(2-methoxy-pyridin-3-yl)methyl]-3,5-dihydro-imidazo[4,5-d]pyridazin-4-one,
2-(piperazin-1-yl)-3-(butyn-1-yl)-5-[(2-fluoro-pyridin-3-yl)methyl]-3,5-dihydro-imidazo[4,5-d]pyridazin-4-one,
2-(piperazin-1-yl)-3-(butyn-1-yl)-5-[(2-fluoro-pyridin-4-yl)methyl]-3,5-dihydro-imidazo[4,5-d]pyridazin-4-one,
2-(piperazin-1-yl)-3-(butyn-1-yl)-5-[(6-fluoro-pyridin-2-yl)methyl]-3,5-dihydro-imidazo[4,5-d]pyridazin-4-one and
2-(piperazin-1-yl)-3-(butyn-1-yl)-5-[(isoquinolin-1-yl)methyl]-3,5-dihydro-imidazo[4,5-d]pyridazin-4-one, the tautomers, the mixtures and the salts thereof.

Most particularly preferred are those compounds wherein $R^1$ denotes a methyl group which is substituted by a fluoronaphthyl, bromonaphthyl, methoxynaphthyl, cyanonaphthyl, dicyanonaphthyl, methylpyridinyl, cyanopyridinyl, dimethylpyrimidinyl, phenylpyrimidinyl, methylbenzoxazolyl, 1-methyl-1H-benzo-triazolyl, benzo[1,2,5]thiadiazolyl, [1,2,4]triazolo[4,3-a]pyridinyl, quinolinyl, fluoroquinolinyl, methylquinolinyl, cyanoquinolinyl, methylisoquinolinyl, cyanoisoquinolinyl, quinazolinyl, methylquinazolinyl, phenylquinazolinyl, (dimethyl-amino)-quinazolinyl, (morpholin-4-yl)-quinazolinyl, quinoxalinyl, dimethylquinoxalinyl, trimethylquinoxalinyl, naphthyridinyl or phenanthridinyl group, $R^2$ denotes a hydrogen atom, $R^3$ denotes a 2-butyn-1-yl group, and n denotes the number 1 or 2, the tautomers, the mixtures and the salts thereof, particularly preferred are those compounds wherein $R^1$ denotes a methyl group which is substituted by a cyanonaphthyl, methylbenzoxazolyl, 1-methyl-1H-benzotriazolyl, benzo[1,2,5]thiadiazolyl, methylisoquinolinyl, methylquinazolinyl or trimethylquinoxalinyl group, $R^2$ denotes a hydrogen atom, $R^3$ denotes a 2-butyn-1-yl group and n denotes the number 1 or 2, the tautomers and the salts thereof.

A preferred sub-group comprises those compounds of general formula I wherein $R^1$, $R^2$ and $R^3$ are as hereinbefore defined and n denotes the number 1, the tautomers and the salts thereof.

A second preferred sub-group comprises those compounds of general formula I wherein $R^1$, $R^2$ and $R^3$ are as hereinbefore defined and n denotes the number 2, the tautomers and the salts thereof.

Particular mention may be made of the following compounds:
(a) 2-(piperazin-1-yl)-3-(2-butyn-1-yl)-5-[(4-methyl-quinazolin-2-yl)methyl]-3,5-dihydro-imidazo[4,5-d]pyridazin-4-one
(b) 2-([1,4]diazepan-1-yl)-3-(2-butyn-1-yl)-5-[(4-methyl-quinazolin-2-yl)methyl]-3,5-dihydro-imidazo[4,5-d]pyridazin-4-one
(c) 2-(piperazin-1-yl)-3-(2-butyn-1-yl)-5-[(4-methyl-benzoxazol-2-yl)methyl]-3,5-dihydro-imidazo[4,5-d]pyridazin-4-one
(d) 2-([1,4]diazepan-1-yl)-3-(2-butyn-1-yl)-5-[(4-methyl-benzoxazol-2-yl)methyl]-3,5-dihydro-imidazo[4,5-d]pyridazin-4-one and the tautomers and salts thereof.

According to the invention the compounds of general formula I are obtained by methods known per se, for example by the following methods:

a) Reacting a Compound of General Formula

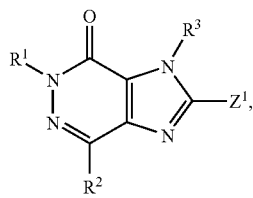

(II)

wherein $R^1$ to $R^3$ are as hereinbefore defined and $Z^1$ denotes a leaving group such as a halogen atom, a substituted hydroxy, mercapto, sulphinyl, sulphonyl or sulphonyloxy group such as a chlorine or bromine atom, a methanesulphonyl or methanesulphonyloxy group, with piperazine or [1,4]diazepan or the salts thereof.

The reaction is expediently carried out in a solvent such as isopropanol, butanol, tetrahydrofuran, dioxane, dimethylformamide, dimethylsulphoxide, ethyleneglycol monomethylether, ethyleneglycol diethylether or sulpholane, optionally in the presence of an inorganic or tertiary organic base, e.g. sodium carbonate, potassium carbonate or potassium hydroxide, a tertiary organic base, e.g. triethylamine, or in the presence of N-ethyl-diisopropylamine (Hünig base), while these organic bases may simultaneously act as solvent, and optionally in the presence of a reaction accelerator such as an alkali metal halide or a palladium-based catalyst at temperatures between −20 and 180° C., but preferably at temperatures between −10 and 120° C. However, the reaction may also be carried out without a solvent or in an excess of piperazine or [1,4]diazepan.

b) Deprotecting a Compound of General Formula

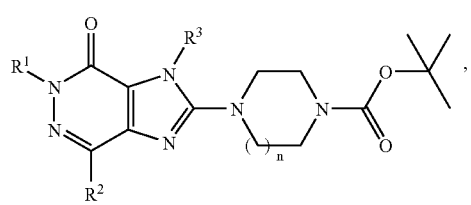

(III)

wherein $R^1$, $R^2$, $R^3$ and n are as hereinbefore defined.

The tert.-butyloxycarbonyl group is preferably cleaved by treating with an acid such as trifluoroacetic acid or hydrochloric acid or by treating with bromotrimethylsilane or iodotrimethylsilane, optionally using a solvent such as methylene chloride, ethyl acetate, dioxane, methanol, isopropanol or diethyl ether at temperatures between 0 and 80° C.

In the reactions described hereinbefore, any reactive groups present such as amino, alkylamino or imino groups may be protected during the reaction by conventional protecting groups which are cleaved again after the reaction.

For example, a protecting group for an amino, alkylamino or imino group may be a formyl, acetyl, trifluoroacetyl, ethoxycarbonyl, tert-butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

However, a benzyl, methoxybenzyl or benzyloxycarbonyl group is cleaved, for example, hydrogenolytically, e.g. with hydrogen in the presence of a catalyst such as palladium/charcoal in a suitable solvent such as methanol, ethanol, ethyl acetate or glacial acetic acid optionally with the addition of an acid such as hydrochloric acid at temperatures between 0 and 100° C., but preferably at ambient temperatures between 20 and 60° C., and at a hydrogen pressure of 1 to 7 bar, but preferably from 3 to 5 bar. However, a 2,4-dimethoxybenzyl group is preferably cleaved in trifluoroacetic acid in the presence of anisole. A tert.-butyl or tert.-butyloxycarbonyl group is preferably cleaved by treating with an acid such as trifluoroacetic acid or hydrochloric acid or by treating with iodotrimethylsilane optionally using a solvent such as methylene chloride, dioxane, methanol or diethyl ether.

A trifluoroacetyl group is preferably cleaved by treating with an acid such as hydrochloric acid optionally in the presence of a solvent such as acetic acid at temperatures between 50 and 120° C. or by treating with sodium hydroxide solution, optionally in the presence of a solvent such as tetrahydrofuran at temperatures between 0 and 50° C.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures obtained may be separated by chromatography into their cis and trans isomers, the compounds of general formula I obtained which occur as racemates may be separated by methods known per se (cf. Allinger N. L. and Eliel E. L. in "Topics in Stereochemistry", Vol. 6, Wiley Interscience, 1971) into their optical enantiomers and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be, for example, (+) or (−)-menthol and an optically active acyl group in amides, for example, may be a (+)- or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

The compounds of general formulae II and III used as starting compounds are either known from the literature or may be prepared by methods known from the literature (see Examples I to XIII).

As already mentioned hereinbefore, the compounds of general formula I according to the invention and the physiologically acceptable salts thereof have valuable pharmacological properties, particularly an inhibiting effect on the enzyme DPP-IV.

The biological properties of the new compounds were investigated as follows:

The ability of the substances and their corresponding salts to inhibit the DPP-IV activity can be demonstrated in an experiment in which an extract of the human colon carcinoma cell line Caco-2 is used as the DPP IV source. The differentiation of the cells in order to induce the DPP-IV expression was carried out in accordance with the description by Reiher et al. in an article entitled "Increased expression of intestinal cell line Caco-2", which appeared in Proc. Natl. Acad. Sci. Vol. 90, pp. 5757–5761 (1993). The cell extract was obtained from cells solubilised in a buffer (10 mM Tris HCl, 0.15 M NaCl, 0.04 t.i.u. aprotinin, 0.5% Nonidet-P40, pH 8.0) by centrifugation at 35,000 g for 30 minutes at 4° C. (to remove cell debris).

The DPP-IV assay was carried out as follows:

50 µl of substrate solution (AFC; AFC is amido-4-trifluoromethylcoumarin), final concentration 100 µM, were placed in black microtitre plates. 20 µl of assay buffer (final concentrations 50 mM Tris HCl pH 7.8, 50 mM NaCl, 1% DMSO) was pipetted in. The reaction was started by the addition of 30 µl of solubilised Caco-2 protein (final concentration 0.14 µg of protein per well). The test substances under investigation were typically added prediluted to 20 µl, while the volume of assay buffer was then reduced accordingly. The reaction was carried out at ambient temperature, the incubation period was 60 minutes. Then the fluorescence was measured in a Victor 1420 Multilabel Counter, with the excitation wavelength at 405 nm and the emission wavelength at 535 nm. Dummy values (corresponding to 0% activity) were obtained in mixtures with no Caco-2 protein (volume replaced by assay buffer), control values (corresponding to 100% activity) were obtained in mixtures without any added substance. The potency of the test substances in question, expressed as $IC_{50}$ values, were calculated from dosage/activity curves consisting of 11 measured points in each case. The following results were obtained:

| Compound (Example No.) | DPP IV inhibition $IC_{50}$ [nM] |
|---|---|
| 1 | 5 |
| 1(1) | 3 |
| 1(2) | 17 |
| 1(9) | 3 |
| 1(11) | 2 |
| 1(12) | 4 |
| 1(13) | 5 |
| 2 | 14 |

The compounds prepared according to the invention are well tolerated as no toxic side effects could be detected in rats after the oral administration of 10 mg/kg of the compound of Example 1, for example.

In view of their ability to inhibit DPP-IV activity, the compounds of general formula I according to the invention and the corresponding pharmaceutically acceptable salts thereof are suitable for influencing any conditions or diseases which can be affected by the inhibition of the DPP-IV activity. It is therefore to be expected that the compounds according to the invention will be suitable for the prevention or treatment of diseases or conditions such as type I and type II diabetes mellitus, pre-diabetes, reduced glucose tolerance or changes in the fasting blood sugar, diabetic complications (e.g. retinopathy, nephropathy or neuropathies), metabolic acidosis or ketosis, reactive hypoglycaemia, insulin resistance, dyslipidaemias of various origins, arthritis, atherosclerosis and related diseases, obesity, allograft transplantation and osteoporosis caused by calcitonin. In addition, these substances are suitable for preventing B-cell degeneration such as e.g. apoptosis or necrosis of pancreatic B-cells. The substances are also suitable for improving or restoring the function of pancreatic cells and additionally increasing the size and number of pancreatic B-cells. Additionally, on the basis of the role of the glucagon-like peptides such as e.g. GLP-1 and GLP-2 and their link with DPP-IV inhibition, it is expected that the compounds according to the invention will be suitable for achieving, inter alia, a sedative or tranquillising effect, as well as having a favourable effect on catabolic states after operations or hormonal stress responses or possibly reducing mortality and morbidity after myocardial infarct. Moreover, they are suitable for treating any conditions connected with the effects mentioned above and mediated by GLP-1 or GLP-2. The compounds according to the invention may also be used as diuretics or antihypertensives and are suitable for preventing and treating acute kidney failure. The compounds according to the invention may also be used to treat inflammatory complaints of the respiratory tract. They are also suitable for preventing and treating chronic inflammatory bowel diseases such as e.g. irritable bowel syndrome (IBS), Crohn's disease or ulcerative colitis and also pancreatitis. It is also expected that they can be used for all kinds of injury or damage to the gastrointestinal tract such as may occur in colitis and enteritis, for example. Moreover, it is expected that DPP-IV inhibitors and hence the compounds according to the invention can be used to treat infertility or to improve fertility in humans or mammals, particularly if the infertility is connected with insulin resistance or with polycystic ovary syndrome. On the other hand these substances are suitable for influencing sperm motility and are thus suitable for use as male contraceptives. In addition, the substances are suitable for treating growth hormone deficiencies connected with restricted growth, and may reasonably be used for all indications for which growth hormone may be used. The compounds according to the invention are also suitable, on the basis of their inhibitory effect on DPP-IV, for treating various autoimmune diseases such as e.g. rheumatoid arthritis, multiple sclerosis, thyroiditis and Basedow's disease, etc. They may also be used to treat viral diseases and also, for example, in HIV infections, for stimulating blood production, in benign prostatic hyperplasia, gingivitis, as well as for the treatment of neuronal defects and neuro-degenerative diseases such as Alzheimer's disease, for example. The compounds described may also be used for the treatment of tumours, particularly for modifying tumour invasion and also metastasisation; examples here are their use in treating T-cell lymphomas, acute lymphoblastic leukaemia, cell-based pancreatic carcinomas, basal cell carcinomas or breast cancers. Other indications are stroke, ischaemia of various origins, Parkinson's disease and migraine. In addition, further indications include follicular and epidermal hyperkeratoses, increased keratinocyte proliferation, psoriasis, encephalo-myelitis, glomerulonephritis, lipodystrophies, as well as psychosomatic, depressive and neuropsychiatric diseases of all kinds.

The compounds according to the invention may also be used in conjunction with other active substances. Suitable therapeutic agents for such combinations include for example antidiabetic agents such as metformin, sulphonylureas (e.g. glibenclamid, tolbutamide, glimepiride), nateglinide, repaglinide, thiazolidinediones (e.g. rosiglitazone, pioglitazone), PPAR-gamma agonists (e.g. GI 262570) and antagonists, PPAR-gamma/alpha modulators (e.g. KRP 297), PPAR-gamma/alpha/delta modulators, AMPK activators, ACC1 and ACC2 inhibitors, DGAT inhibitors, SMT3 receptor agonists, 11β-HSD inhibitors, FGF19 agonists or mimetics, alpha-glucosidase inhibitors (e.g. acarbose, voglibose), other DPPIV inhibitors, alpha2 antagonists, insulin and insulin analogues, GLP-1 and GLP-1 analogues (e.g. exendin-4) or amylin. Also, SGLT2 inhibitors such as T-1095 or KGT-1251 (869682), inhibitors of protein tyrosine phosphatase 1, substances which influence deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents, such as HMG-CoA-reductase inhibitors (e.g. simvastatin, atorvastatin), fibrates (e.g. bezafibrate, fenofibrate), nicotinic acid and its derivatives, PPAR-alpha agonists, PPAR-delta agonists, ACAT inhibitors (e.g. avasimibe) or cholesterol absorption inhibitors such as for example ezetimibe, bile acid-binding substances such as for example cholestyramine, inhibitors of ileac bile acid transport, HDL-raising compounds such as for example inhibitors of CETP or regulators of ABC1 or LXRalpha antagonists, LXRbeta agonists or LXRalpha/beta regulators or active substances for the treatment of obesity, such as e.g. sibutramine or tetrahydrolipostatin, dexfenfluramine, axokine, antagonists of the cannabinoid1 receptor, MCH-1 receptor antagonists, MC4 receptor agonists, NPY5 or NPY2 antagonists or $β_3$-agonists such as SB-418790 or AD-9677 as well as agonists of the 5HT2c receptor.

It is also possible to combine the compounds with drugs for treating high blood pressure such as e.g. AII antagonists or ACE inhibitors, diuretics, β-blockers, Ca-antagonists, etc., or combinations thereof.

The dosage required to achieve such an effect is expediently, by intravenous route, 1 to 100 mg, preferably 1 to 30 mg, and by oral route 1 to 1000 mg, preferably 1 to 100 mg, in each case 1 to 4 times a day. For this purpose, the compounds of formula I prepared according to the invention, optionally combined with other active substances, may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof into conventional galenic preparations such as plain or coated tablets, capsules, powders, suspensions or suppositories.

The Examples that follow are intended to illustrate the invention:

Preparation of the starting compounds:

EXAMPLE I 2-bromo-3-(2-butyn-1-yl)-5-[(4-methyl-quinazolin-2-yl)methyl]-3,5-dihydro-imidazo[4,5-d]pyridazin-4-one A mixture of 20.00 g of 2-bromo-3-(2-butyn-1-yl)-3,5-dihydro-imidazo[4,5-d]pyridazin-4-one, 17.49 g of 2-chloromethyl-4-methyl-quinazoline and 20.93 g of potassium carbonate in 150 ml N-methyl-pyrrolidone is stirred at 80° C. for approx. three hours. After cooling to ambient temperature the reaction mixture is combined with 200 ml water and cooled to 15° C. The precipitate formed is suction filtered, washed with water and dried at 50° C. in the circulating air dryer. The brownish solid is triturated with 100 ml methylene chloride and 50 ml methanol, suction filtered, washed with a little methylene chloride/methanol (2:1) and dried.

Yield: 23.80 g (75% of theory)

$R_f$ value: 0.35 (silica gel, methylene chloride/ethanol=19:1)

Mass spectrum (ESI$^+$): m/z=423, 425 [M+H]$^+$

The following compounds are obtained analogously to Example 1:

(1) 2-(4-tert.-butyloxycarbonyl-piperazin-1-yl)-3-(2-butyn-1-yl)-5-[(2,3,8-trimethyl-quinoxalin-6-yl)methyl]-3,5-dihydro-imidazo[4,5-d]pyridazin-4-one Mass spectrum (ESI$^+$): m/z=557 [M$^+$H]$^+$ (2) 2-bromo-3-(2-butyn-1-yl)-5-[(2,3,8-trimethyl-quinoxalin-6-yl)methyl]-3,5-dihydro-imidazo[4,5-d]pyridazin-4-one (3) 2-bromo-3-(2-butyn-1-yl)-5-[(4-cyano-naphthalen-1-yl)methyl]-3,5-dihydro-imidazo[4,5-d]pyridazin-4-one Mass spectrum (ESI$^+$): m/z=432, 434 [M+H]$^+$ (4) 2-bromo-3-(2-butyn-1-yl)-5-[(4-fluoro-naphthalen-1-yl)methyl]-3,5-dihydro-imidazo[4,5-d]pyridazin-4-one (5) 2-bromo-3-(2-butyn-1-yl)-5-[(4-bromo-naphthalen-1-yl)methyl]-3,5-dihydro-imidazo[4,5-d]pyridazin-4-one $R_f$ value: 0.90 (silica gel, methylene chloride/ethanol/conc. aqueous ammonia=90:10:1)

(6) 2-bromo-3-(2-butyn-1-yl)-5-[(4-methyl-benzoxazol-2-yl)methyl]-3,5-dihydro-imidazo[4,5-d]pyridazin-4-one $R_f$ value: 0.70 (silica gel, methylene chloride/ethanol/conc. aqueous ammonia=90:10:1)

(7) 2-bromo-3-(2-butyn-1-yl)-5-[([1,2,4]triazolo[4,3-a]pyridin-3-yl)methyl]-3,5-dihydro-imidazo[4,5-d]pyridazin-4-one $R_f$ value: 0.70 (silica gel, methylene chloride/ethanol/conc.aqueous ammonia=90:10:1)

(8) 2-bromo-3-(2-butyn-1-yl)-5-[(1-methyl-1H-benzotriazol-5-yl)methyl]-3,5-dihydro-imidazo[4,5-d]pyridazin-4-one $R_f$ value: 0.30 (silica gel, methylene chloride/ethanol=19:1)

(9) 2-bromo-3-(2-butyn-1-yl)-5-[(4-methyl-pyridin-2-yl)methyl]-3,5-dihydro-imidazo[4,5-d]pyridazin-4-one $R_f$ value: 0.40 (silica gel, methylene chloride/ethanol=19:1)

(10) 2-bromo-3-(2-butyn-1-yl)-5-[(benzo[1,2,5]thiadiazol-5-yl)methyl]-3,5-dihydro-imidazo[4,5-d]pyridazin-4-one $R_f$ value: 0.38 (silica gel, methylene chloride/ethanol=19:1)

(11) 2-bromo-3-(2-butyn-1-yl)-5-[(3-methyl-isoquinolin-1-yl)methyl]-3,5-dihydro-imidazo[4,5-d]pyridazin-4-one $R_f$ value: 0.40 (silica gel, methylene chloride/methanol=95:5)

Mass spectrum (ESI$^+$): m/z=422, 424 [M+H]$^+$

(12) 2-bromo-3-(2-butyn-1-yl)-5-[(1,5-naphthyridin-2-yl)methyl]-3,5-dihydro-imidazo[4,5-d]pyridazin-4-one Mass spectrum (ESI$^+$): m/z=409, 411 [M+H]$^+$

(13) 2-bromo-3-(2-butyn-1-yl)-5-[(4-cyano-isoquinolin-1-yl)methyl]-3,5-dihydro-imidazo[4,5-d]pyridazin-4-one The 1-bromomethyl-4-cyano-isoquinoline used (mass spectrum (ESI$^+$): m/z=247, 249 [M+H]$^+$) is obtained by brominating 1-methyl-4-cyano-isoquinoline with N-bromosuccinimide in carbon tetrachloride in the presence of 2,2'-azobis-(isobutyronitrile).

Mass spectrum (ESI$^+$): m/z=433, 435 [M+H]$^+$

(14) 2-bromo-3-(2-butyn-1-yl)-5-[(quinoxalin-6-yl)methyl]-3,5-dihydro-imidazo[4,5-d]pyridazin-4-one Mass spectrum (ESI$^+$): m/z=409, 411 [M+H]$^+$

EXAMPLE II 2-bromo-3-(2-butyn-1-yl)-3,5-dihydro-imidazo[4,5-d]pyridazin-4-one 0.31 ml hydrazine hydrate (99%), dissolved in 1 ml of ethanol, is added dropwise at ambient temperature to a solution of 1.80 g of methyl 2-bromo-3-(2-butyn-1-yl)-5-formyl-3H-imidazol-4-carboxylate in 25 ml of ethanol. Five minutes later 1.5 ml of concentrated acetic acid are added and the mixture is refluxed for 30 minutes. After cooling the solid precipitated is suction filtered, washed with 10 ml of ethanol and 20 ml of diethyl ether and dried.

Yield: 1.25 g (74% of theory)

Mass spectrum (ESI$^+$): m/z=267, 269 [M+H]$^+$

1H-NMR spectrum (d6-DMSO): δ=1.80 (s, 3H); 5.28 (s, 2H); 8.38 (s, 1H); 12.99 (s, 1H) ppm

EXAMPLE III

Methyl 2-bromo-3-(2-butyn-1-yl)-5-formyl-3H-imidazol-4-carboxylate 43 ml of a 1 M solution of diisobutyl-aluminium hydride in tetrahydrofuran are added dropwise within 20 minutes to a solution of 13.5 g of dimethyl 2-bromo-1-(2-butyn-1-yl)-1H-imidazole-4,5-dicarboxylate in 220 ml of tetrahydrofuran under an argon atmosphere at −70° C. The mixture is stirred for a further four hours at −70° C., then 20 ml of a mixture of 1M hydrochloric acid and tetrahydrofuran are added dropwise. After heating to ambient temperature approx. 200 ml of water are added and the mixture is extracted three times with 70 ml of ethyl acetate. The combined extracts are dried and evaporated down. The crude product thus obtained is purified by column chromatography over silica gel with petroleum ether/ethyl acetate (80:20 to 50:50) as eluant.

Yield: 6.40 g (52% of theory)

Mass spectrum (ESI$^+$): m/z=285, 287 [M+H]$^+$

1H-NMR spectrum (d6-DMSO): δ=1.80 (s, 3H); 3.93 (s, 3H); 5.11 (s, 2H); 10.12 (s, 1H) ppm

EXAMPLE IV

Dimethyl 2-bromo-1-(2-butyn-1-yl)-1H-imidazole-4,5-dicarboxylate

A solution of 15.0 g of dimethyl 2-bromo-imidazole-4,5-dicarboxylate, 5.15 ml of 1-bromo-2-butyne and 50 ml of N,N-diisopropylethylamine in 280 ml of tetrahydrofuran is refluxed for one hour. The mixture is concentrated by evaporation, the residue is combined with approx. 100 ml of water and extracted three times with 70 ml of ethyl acetate. The extracts are washed with 50 ml of water, dried and evaporated down. The crude product thus obtained is purified by column chromatography over silica gel with methylene chloride/ethanol (100:0 auf 98:2) as eluant.

Yield: 13.50 g (75% of theory)

$R_f$ value: 0.82 (silica gel, methylene chloride/ethanol=9:1)

Mass spectrum (ESI$^+$): m/z=315, 317 [M+H]$^+$

EXAMPLE V 2-(4-tert.-butyloxycarbonyl-piperazin-1-yl)-3-(2-butyn-1-yl)-3,5-dihydro-imidazo[4,5-d]pyridazin-4-one A mixture of 2.11 g of 2-bromo-3-(2-butyn-1-yl)-3,5-dihydro-imidazo[4,5-d]pyridazin-4-one, 1.64 g potassium carbonate and 1.91 g 1-tert.-butyloxycarbonyl-piperazine in 20 ml N,N-dimethylformamide is stirred for six hours at 80° C. After cooling to ambient temperature the reaction mixture is combined with water and the precipitate formed is suction filtered. The crude product is purified by chromatography over a silica gel column with methylene chloride/methanol (95:5 to 90:10).

Yield: 1.94 g (66% of theory)

Mass spectrum (ESI$^+$): m/z=373 [M+H]$^+$

EXAMPLE VI 6-chloromethyl-2,3,8-trimethyl-quinoxaline-hydrochloride

Prepared by treating (2,3,8-trimethyl-quinoxalin-6-yl)-methanol with thionyl chloride in methylene chloride.

$R_f$ value: 0.81 (silica gel, ethyl acetate/petroleum ether=1:1)

Mass spectrum (ESI$^+$: m/z=221, 223 [M+H]$^+$

The following compounds are obtained analogously to Example VI:

(1) 3-chloromethyl-[1,2,4]triazolo[4,3-a]pyridine $R_f$ value: 0.50 (silica gel, methylene chloride/ethanol=9:1)

EXAMPLE VII (2,3,8-trimethyl-quinoxalin-6-yl)-methanol

Prepared by reducing 691 mg of methyl 2,3,8-trimethyl-quinoxaline-6-carboxylate with 300 mg of lithium aluminium hydride (95%) in 15 ml tetrahydrofuran at ambient temperature.

Yield: 368 mg (61% of theory)

Mass spectrum (ESI$^+$): m/z=203 [M+H]$^+$

EXAMPLE VIII

Methyl 2,3,8-trimethyl-quinoxaline-6-carboxylate

Prepared by reacting 1.60 g of methyl 3,4-diamino-5-methyl-benzoate with 0.86 ml diacetyl in a mixture of water and ethanol at reflux temperature.

Yield: 1.53 g (80% of theory)
$R_f$ value: 0.63 (silica gel, cyclohexane/ethyl acetate=1:1)
Mass spectrum (ESI$^+$): m/z=231 [M+H]$^+$

EXAMPLE IX

Methyl 3,4-diamino-5-methyl-benzoate

Prepared by reducing methyl 3-nitro-4-amino-5-methyl-benzoate at a partial hydrogen pressure of 50 psi in the presence of Raney nickel in methanol at ambient temperature.

$R_f$ value: 0.40 (silica gel, tert.-butylmethylether)

EXAMPLE X

Methyl 3-nitro-4-amino-5-methyl-benzoate

Prepared by treating 3-nitro-4-acetylamino-5-methyl-benzoic acid with hydrogen chloride gas in methanol at ambient temperature and subsequently heating to reflux temperature.

$R_f$ value: 0.75 (silica gel, tert.-butylmethylether/acetic acid=99:1)

Mass spectrum (ESI$^+$): m/z=211 [M+H]$^+$

EXAMPLE XI

[1,2,4]triazolo[4,3-a]pyridin-3-yl-methanol

Prepared by treating 5.40 g of 3-acetoxymethyl-[1,2,4]triazolo[4,3-a]pyridine with 30 ml of 2 N sodium hydroxide solution in 50 ml of ethanol at ambient temperature.

Yield: 3.20 g (76% of theory)
$R_f$ value: 0.30 (silica gel, methylene chloride/ethanol=9:1)
Mass spectrum (ESI$^+$): m/z=150 [M+H]$^+$

EXAMPLE XII

3-Acetoxymethyl-[1,2,4]triazolo[4,3-a]pyridine

Prepared by heating 8.00 g (N'-pyridin-2-yl)hydrazinocarbonylmethyl acetate in 100 ml of glacial acetic acid at reflux temperature.

Yield: 5.40 g (74% of theory)
$R_f$ value: 0.60 (silica gel, methylene chloride/ethanol=9:1)
Mass spectrum (ESI$^+$): m/z=192 [M+H]$^+$

EXAMPLE XIII (N'-Pyridin-2-yl)hydrazinocarbonylmethyl acetate 4.30 ml of acetoxyacetyl chloride are added dropwise to a mixture of 4.37 g of 2-hydrazino-pyridine and 6.97 ml of triethylamine in 100 ml of tetrahydrofuran at ambient temperature with stirring. Then the reaction mixture is stirred for another two hours at ambient temperature. The mixture is then evaporated down and the residue is chromatographed through a silica gel column with methylene chloride/methanol (100:0 to 95:5) as eluant.

Yield: 8.00 g (96% of theory)
$R_f$ value: 0.40 (silica gel, methylene chloride/ethanol=9:1)
Mass spectrum (ESI$^+$): m/z=210 [M+H]$^+$ Preparation of the final compounds:

EXAMPLE I 2-(piperazin-1-yl)-3-(2-butyn-1-yl)-5-[(4-methyl-quinazolin-2-yl)methyl]-3,5-dihydro-imidazo[4,5-d]pyridazin-4-one A mixture of 300 mg of 2-bromo-3-(2-butyn-1-yl)-5-[(4-methyl-quinazolin-2-yl)methyl]-3,5-dihydro-imidazo[4,5-d]pyridazin-4-one and 300 mg of piperazine in 5 ml of N,N-dimethylformamide is heated for five minutes in the microwave to 200° C. Then the solvent is distilled off in vacuo. The residue is dissolved in methylene chloride, combined with water and extracted with methylene chloride.

The combined organic phases are washed with saturated sodium chloride solution, dried over magnesium sulphate and evaporated down. The crude product is purified by chromatography through a silica gel column with methylene chloride/methanol/conc. methanolic ammonia (99:0.9:0.1 to 90:9:1) as eluant.

Yield: 155 mg (51% of theory)
$R_f$ value: 0.60 (Reversed phase ready-made TLC plate (E. Merck), acetonitrile/water/trifluoroacetic acid=50:50:1)
Mass spectrum (ESI$^+$): m/z=429 [M+H]$^+$ The following compounds are obtained analogously to Example 1:

(1) 2-([1,4]diazepan-1-yl)-3-(2-butyn-1-yl)-5-[(4-methyl-quinazolin-2-yl)methyl]-3,5-dihydro-imidazo[4,5-d]pyridazin-4-one melting point: 175–178° C.
Mass spectrum (ESI$^+$): m/z=443 [M+H]$^+$ (2) 2-([1,4]diazepan-1-yl)-3-(2-butyn-1-yl)-5-[(2,3,8-trimethyl-quinoxalin-6-yl)methyl]-3,5-dihydro-imidazo[4,5-d]pyridazin-4-one Mass spectrum (ESI$^+$): m/z=471 [M+H]$^+$ (3) 2-([1,4]diazepan-1-yl)-3-(2-butyn-1-yl)-5-[(4-cyano-naphthalen-1-yl)methyl]-3,5-dihydro-imidazo[4,5-d]pyridazin-4-one Mass spectrum (ESI$^+$): m/z=452 [M+H]$^+$ (4) 2-(piperazin-1-yl)-3-(2-butyn-1-yl)-5-[(4-cyano-naphthalen-1-yl)methyl]-3,5-dihydro-imidazo[4,5-d]pyridazin-4-one Mass spectrum (ESI$^+$): m/z=438 [M+H]$^+$ (5) 2-(piperazin-1-yl)-3-(2-butyn-1-yl)-5-[(4-fluoro-naphthalen-1-yl)methyl]-3,5-dihydro-imidazo[4,5-d]pyridazin-4-one $R_f$ value: 0.15 (silica gel, methylene chloride/ethanol=9:1)
Mass spectrum (ESI$^+$): m/z=431 [M+H]$^+$ (6) 2-([1,4]diazepan-1-yl)-3-(2-butyn-1-yl)-5-[(4-fluoro-naphthalen-1-yl)methyl]-3,5-dihydro-imidazo[4,5-d]pyridazin-4-one R$_f$ value: 0.1 (silica gel, methylene chloride/ethanol=9:1)
Mass spectrum (ESI$^+$): m/z=445 [M+H]$^+$ (7) 2-(piperazin-1-yl)-3-(2-butyn-1-yl)-5-[(4-bromo-naphthalen-1-yl)methyl]-3,5-dihydro-imidazo[4,5-d]pyridazin-4-one R$_f$ value: 0.25 (silica gel, methylene chloride/ethanol/conc.aqueous ammonia=90:10:1)
Mass spectrum (ESI$^+$): m/z=491, 493 [M+H]$^+$ (8) 2-([1,4]diazepan-1-yl)-3-(2-butyn-1-yl)-5-[(4-bromo-naphthalen-1-yl)methyl]-3,5-dihydro-imidazo[4,5-d]pyridazin-4-one R$_f$ value: 0.35 (silica gel, methylene chloride/ethanol/conc.aqueous ammonia=90:10:1)
Mass spectrum (ESI$^+$): m/z=505, 507 [M+H]$^+$ (9) 2-(piperazin-1-yl)-3-(2-butyn-1-yl)-5-[(4-methyl-benzoxazol-2-yl)methyl]-3,5-dihydro-imidazo[4,5-d]pyridazin-4-one R$_f$ value: 0.30 (silica gel, methylene chloride/ethanol/conc.aqueous ammonia=90:10:1)
Mass spectrum (ESI$^+$): m/z=418 [M+H]$^+$

(10) 2-(piperazin-1-yl)-3-(2-butyn-1-yl)-5-[(1,2,4]triazolo[4,3-a]pyridin-3-yl)methyl]-3,5-dihydro-imidazo[4,5-d]pyridazin-4-one R$_f$ value: 0.20 (silica gel, methylene chloride/ethanol/conc.aqueous ammonia=90:10:1)
Mass spectrum (ESI$^+$): m/z=404 [M+H]$^+$

(11) 2-(piperazin-1-yl)-3-(2-butyn-1-yl)-5-[(1-methyl-1H-benzotriazol-5-yl)methyl]-3,5-dihydro-imidazo[4,5-d]pyridazin-4-one R$_f$ value: 0.40 (silica gel, methylene chloride/ethanol/conc.aqueous ammonia=90:10:1)
Mass spectrum (ESI$^+$): m/z=418 [M+H]$^+$

(12) 2-([1,4]diazepan-1-yl)-3-(2-butyn-1-yl)-5-[(1-methyl-1H-benzotriazol-5-yl)methyl]-3,5-dihydro-imidazo[4,5-d]pyridazin-4-one R$_f$ value: 0.15 (silica gel, methylene chloride/ethanol/conc.aqueous ammonia=90:10:1)
Mass spectrum (ESI$^+$): m/z=432 [M+H]$^+$

(13) 2-([1,4]diazepan-1-yl)-3-(2-butyn-1-yl)-5-[(4-methyl-benzoxazol-2-yl)methyl]-3,5-dihydro-imidazo[4,5-d]pyridazin-4-one R$_f$ value: 0.30 (silica gel, methylene chloride/ethanol/conc.aqueous ammonia=90:10:1)
Mass spectrum (ESI$^+$): m/z=432 [M+H]$^+$

(14) 2-([1,4]diazepan-1-yl)-3-(2-butyn-1-yl)-5-[(1,2,4]triazolo[4,3-a]pyridin-3-yl)methyl]-3,5-dihydro-imidazo[4,5-d]pyridazin-4-one R$_f$ value: 0.15 (silica gel, methylene chloride/ethanol/conc.aqueous ammonia=90:10:1)
Mass spectrum (ESI$^+$): m/z=418 [M+H]$^+$

(15) 2-(piperazin-1-yl)-3-(2-butyn-1-yl)-5-[(4-methyl-pyridin-2-yl)methyl]-3,5-dihydro-imidazo[4,5-d]pyridazin-4-one R$_f$ value: 0.80 (aluminium oxide, methylene chloride/ethanol=9:1)
Mass spectrum (ESI$^+$): m/z=378 [M+H]$^+$

(16) 2-([1,4]diazepan-1-yl)-3-(2-butyn-1-yl)-5-[(4-methyl-pyridin-2-yl)methyl]-3,5-dihydro-imidazo[4,5-d]pyridazin-4-one R$_f$ value: 0.75 (aluminium oxide, methylene chloride/ethanol=9:1)
Mass spectrum (ESI$^+$): m/z=392 [M+H]$^+$

(17) 2-(piperazin-1-yl)-3-(2-butyn-1-yl)-5-[(benzo[1,2,5]thiadiazol-5-yl)methyl]-3,5-dihydro-imidazo[4,5-d]pyridazin-4-one R$_f$ value: 0.55 (aluminium oxide, methylene chloride/ethanol=19:1)
Mass spectrum (ESI+): m/z=421 [M+H]$^+$

(18) 2-([1,4]diazepan-1-yl)-3-(2-butyn-1-yl)-5-[(benzo[1,2,5]thiadiazol-5-yl)methyl]-3,5-dihydro-imidazo[4,5-d]pyridazin-4-one R$_f$ value: 0.45 (aluminium oxide, methylene chloride/ethanol=19:1)
Mass spectrum (ESI$^+$): m/z=435 [M+H]$^+$

(19) 2-(piperazin-1-yl)-3-(2-butyn-1-yl)-5-[(3-methyl-isoquinolin-1-yl)methyl]-3,5-dihydro-imidazo[4,5-d]pyridazin-4-one Mass spectrum (ESI$^+$): m/z=428 [M+H]$^+$

(20) 2-([1,4]diazepan-1-yl)-3-(2-butyn-1-yl)-5-[(3-methyl-isoquinolin-1-yl)methyl]-3,5-dihydro-imidazo[4,5-d]pyridazin-4-one Mass spectrum (ESI$^+$): m/z=442 [M+H]$^+$

(21) 2-([1,4]diazepan-1-yl)-3-(2-butyn-1-yl)-5-[(1,5-naphthyridin-2-yl)methyl]-3,5-dihydro-imidazo[4,5-d]pyridazin-4-one Mass spectrum (ESI$^+$): m/z=429 [M+H]$^+$

(22) 2-([1,4]diazepan-1-yl)-3-(2-butyn-1-yl)-5-[(4-cyano-isoquinolin-1-yl)methyl]-3,5-dihydro-imidazo[4,5-d]pyridazin-4-one Mass spectrum (ESI$^+$): m/z=453 [M+H]$^+$

(23) 2-(piperazin-1-yl)-3-(2-butyn-1-yl)-5-[(4-cyano-isoquinolin-1-yl)methyl]-3,5-dihydro-imidazo[4,5-d]pyridazin-4-one Mass spectrum (ESI$^+$): m/z=439 [M+H]$^+$

(24) 2-(piperazin-1-yl)-3-(2-butyn-1-yl)-5-[(quinoxalin-6-yl)methyl]-3,5-dihydro-imidazo[4,5-d]pyridazin-4-one Mass spectrum (ESI$^+$): m/z=415 [M+H]$^+$

EXAMPLE 2

2-(piperazin-1-yl)-3-(2-butyn-1-yl)-5-[(2,3,8-trimethyl-quinoxalin-6-yl)methyl]-3,5-dihydro-imidazo[4,5-d]pyridazin-4-one 2 ml of trifluoroacetic acid are added to 220 mg of 2-(4-tert.-butyloxycarbonyl-piperazin-1-yl)-3-(2-butyn-1-yl)-5-[(2,3,8-trimethyl-quinoxalin-6-yl)methyl]-3,5-dihydro-imidazo[4,5-d]pyridazin-4-one in 4 ml methylene chloride. The reaction mixture is stirred for one hour at ambient temperature. Then it is diluted with methylene chloride and washed with saturated sodium hydrogen carbonate solution. The organic phase is dried and evaporated down. The glassy residue is dissolved in dioxane, frozen with liquid nitrogen and dried at 6×10$^{-3}$ mbar. A white solid remains.

Yield: 165 mg (91% of theory)
Mass spectrum (ESI$^+$): m/z=457 [M+H]$^+$

The following compounds may also be obtained analogously to the foregoing Examples and other methods known from the literature:

2-(piperazin-1-yl)-3-(2-butyn-1-yl)-5-[(4-methoxy-naphthalen-1-yl)methyl]-3,5-dihydro-imidazo[4,5-d]pyridazin-4-one 2-(piperazin-1-yl)-3-(2-butyn-1-yl)-5-[(4-dimethylamino-quinazolin-2-yl)methyl]-3,5-dihydro-imidazo[4,5-d]pyridazin-4-one 2-(piperazin-1-yl)-3-(2-butyn-1-yl)-5-{[4-(morpholin-4-yl)-quinazolin-2-yl]methyl}-3,5-dihydro-imidazo[4,5-d]pyridazin-4-one 2-(piperazin-1-yl)-3-(2-butyn-1-yl)-5-[([1,5]naphthyridin-2-yl)methyl]-3,5-dihydro-imidazo[4,5-d]pyridazin-4-one 2-(piperazin-1-yl)-3-(2-butyn-1-yl)-5-[([1,5]naphthyridin-3-yl)methyl]-3,5-dihydro-imidazo[4,5-d]pyridazin-4-one 2-(piperazin-1-yl)-3-(2-butyn-1-yl)-5-[(2-methyl-quinolin-4-yl)methyl]-3,5-dihydro-imidazo[4,5-d]pyridazin-4-one 2-(piperazin-1-yl)-3-(2-butyn-1-yl)-5-[(7-fluoro-quinolin-2-yl)methyl]-3,5-dihydro-imidazo[4,5-d]pyridazin-4-one
2-(piperazin-1-yl)-3-(2-butyn-1-yl)-5-[(4-phenyl-pyrimidin-2-yl)methyl]-3,5-dihydro-imidazo[4,5-d]pyridazin-4-one
2-(piperazin-1-yl)-3-(2-butyn-1-yl)-5-[(1-cyano-isoquinolin-3-yl)methyl]-3,5-dihydro-imidazo[4,5-d]pyridazin-4-one
2-(piperazin-1-yl)-3-(2-butyn-1-yl)-5-[(4-cyano-isoquinolin-1-yl)methyl]-3,5-dihydro-imidazo[4,5-d]pyridazin-4-one
2-(piperazin-1-yl)-3-(2-butyn-1-yl)-5-[(quinazolin-6-yl)methyl]-3,5-dihydro-imidazo[4,5-d]pyridazin-4-one
2-(piperazin-1-yl)-3-(2-butyn-1-yl)-5-[(isoquinolin-1-yl)methyl]-3,5-dihydro-imidazo[4,5-d]pyridazin-4-one
2-(piperazin-1-yl)-3-(2-butyn-1-yl)-5-[(quinolin-4-yl)methyl]-3,5-dihydro-imidazo[4,5-d]pyridazin-4-one
2-(piperazin-1-yl)-3-(2-butyn-1-yl)-5-[(3-cyano-quinolin-2-yl)methyl]-3,5-dihydro-imidazo[4,5-d]pyridazin-4-one
2-(piperazin-1-yl)-3-(2-butyn-1-yl)-5-[(1,4-dicyano-naphthalen-2-yl)methyl]-3,5-dihydro-imidazo[4,5-d]pyridazin-4-one
2-(piperazin-1-yl)-3-(2-butyn-1-yl)-5-[(phenanthridin-6-yl)methyl]-3,5-dihydro-imidazo[4,5-d]pyridazin-4-one
2-(piperazin-1-yl)-3-(2-butyn-1-yl)-5-[(2,3-dimethyl-quinoxalin-6-yl)methyl]-3,5-dihydro-imidazo[4,5-d]pyridazin-4-one
2-(piperazin-1-yl)-3-(2-butyn-1-yl)-5-[(4-phenyl-quinazolin-2-yl)methyl]-3,5-dihydro-imidazo[4,5-d]pyridazin-4-one
2-(piperazin-1-yl)-3-(2-butyn-1-yl)-5-[(3-cyano-pyridin-2-yl)methyl]-3,5-dihydro-imidazo[4,5-d]pyridazin-4-one
2-(piperazin-1-yl)-3-(2-butyn-1-yl)-5-[(4,6-dimethyl-pyrimidin-2-yl)methyl]-3,5-dihydro-imidazo[4,5-d]pyridazin-4-one

EXAMPLE 3

Coated Tablets Containing 75 mg of Active Substance
1 tablet core contains:

| | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks about 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.
Weight of core: 230 mg
die: 9 mm, convex The tablet cores thus produced are coated with a film consisting essentially of hydroxypropylmethylcellulose. The finished film-coated tablets are polished with beeswax.
Weight of coated tablet: 245 mg.

EXAMPLE 4

Tablets Containing 100 mg of Active Substance
Composition:
1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.
Weight of tablet: 220 mg
Diameter: 10 mm, biplanar, facetted on both sides and notched on one side.

EXAMPLE 5

Tablets Containing 150 mg of Active Substance
Composition:
1 tablet contains:

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.
Weight of tablet: 300 mg
die: 10 mm, flat

EXAMPLE 6

Hard Gelatine Capsules Containing 150 mg of Active Substance
1 capsule contains:

| | | |
|---|---|---|
| active substance | | 150.0 mg |
| corn starch (dried) | approx. | 180.0 mg |
| lactose (powdered) | approx. | 87.0 mg |

-continued

| | |
|---|---|
| magnesium stearate | 3.0 mg |
| approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

EXAMPLE 7

Suppositories Containing 150 mg of Active Substance 1 suppository contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE 8

Suspension Containing 50 mg of Active Substance 100 ml of suspension contain:

| | |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water | ad 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

EXAMPLE 9

Ampoules Containing 10 mg Active Substance

Composition:

| | |
|---|---|
| active substance | 10.0 mg |
| 0.01 N hydrochloric acid q.s. | |
| double-distilled water | ad 2.0 ml |

Preparation:

The active substance is dissolved in the necessary amount of 0.01 N HCl, made isotonic with common salt, filtered sterile and transferred into 2 ml ampoules.

EXAMPLE 10

Ampoules Containing 50 mg of Active Substance

Composition:

| | |
|---|---|
| active substance | 50.0 mg |
| 0.01 N hydrochloric acid q.s. | |
| double-distilled water | ad 10.0 ml |

Preparation:

The active substance is dissolved in the necessary amount of 0.01 N HCl, made isotonic with common salt, filtered sterile and transferred into 10 ml ampoules.

What is claimed is:

1. A compound formula (I):

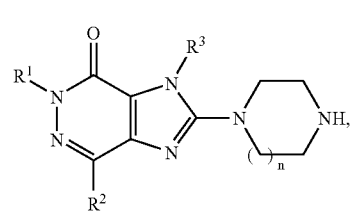

wherein $R^1$ denotes a heteroaryl-$C_{1-3}$-alkyl group, where the term heteroaryl denotes a pyridinyl, pyrimidinyl, phenylpyridinyl, phenylpyrimidinyl, benzoxazolyl, 1-methyl-1H-benzotriazolyl, benzo[1,2,5]thiadiazolyl, [1,2,4]triazolo[4,3-a]pyridinyl, quinolinyl, isoquinolinyl, quinazolinyl, quinoxalinyl, or naphthyridinyl group, and each heteroaryl group is substituted by $R^{10}$ and $R^{11}$, where $R^{10}$ denotes a fluorine, chlorine or bromine atom or a difluoromethyl, trifluoromethyl, cyano, methoxy, difluoromethoxy, trifluoromethoxy, amino, methylamino, dimethylamino, pyrrolidin-1-yl, piperidin-1-yl or morpholin-4-yl group, and $R^{11}$ denotes a methoxy or cyano group or $R^1$ denotes a naphthyl-$C_{1-3}$-alkyl group wherein the naphthyl moiety is substituted by $R^{13}$ wherein $R^{13}$ denotes a difluoromethyl, trifluoromethyl, difluoromethoxy or trifluoromethoxy group, $R^2$ denotes a hydrogen atom or a methyl group, $R^3$ denotes a 2-butyn-1-yl group or a 1-buten-1-yl, 2-buten-1-yl or 3-methyl-2-buten-1-yl group, and n denotes the number 1 or 2, or a tautomer, enantiomer, diastereomer, mixture or salt thereof, with the exception of the compounds:

2-(piperazin-1-yl)-3-(butyn-1-yl)-5-[(pyridin-2-yl)methyl]-3,5-dihydro-imidazo[4,5-d]pyridazin-4-one, 2-(piperazin-1-yl)-3-(butyn-1-yl)-5-[(pyridin-3-yl)methyl]-3,5-dihydro-imidazo[4,5-d]pyridazin-4-one, 2-(piperazin-1-yl)-3-(butyn-1-yl)-5-[(pyridin-4-yl)methyl]-3,5-dihydro-imidazo[4,5-d]pyridazin-4-one, 2-(piperazin-1-yl)-3-(butyn-1-yl)-5-[(2-methoxy-pyridin-3-yl)methyl]-3,5-dihydro-imidazo[4,5-d]pyridazin-4-one, 2-(piperazin-1-yl)-3-(butyn-1-yl)-5-[(6-amino-pyridin-3-yl)methyl]-3,5-dihydro-imidazo[4,5-d]pyridazin-4-one, 2-(piperazin-1-yl)-3-(butyn-1-yl)-5-[(5-amino-pyridin-2-yl)methyl]-3,5-dihydro-imidazo[4,5-d]pyridazin-4-one, 2-(piperazin-1-yl)-3-(butyn-1-yl)-5-[(2-fluoro-pyridin-3-yl)methyl]-3,5-dihydro-imidazo[4,5-d]pyridazin-4-one, 2-(piperazin-1-yl)-3-(butyn-1-yl)-5-[(2-fluoro-pyridin-4-yl)methyl]-3,5-dihydro-imidazo[4,5-d]pyridazin-4-one, 2-(piperazin-1-yl)-3-(butyn-1-yl)-5-[(6-fluoro-pyridin-2-yl)methyl]-3,5-dihydro-imidazo[4,5-d]pyridazin-4-one and 2-(piperazin-1-yl)-3-(butyn-1-yl)-5-[(isoquinolin-1-yl)methyl]-3,5-dihydro-imidazo[4,5-d]pyridazin-4-one.

2. A compound of formula I according to claim 1, wherein:

$R^1$ denotes a heteroarylmethyl group, where the term heteroaryl denotes a pyridinyl, pyrimidinyl, benzoxazolyl, 1-methyl-1H-benzotriazolyl, benzo[1,2,5]thiadiazolyl, [1,2,4]-triazolo[4,3-a]pyridinyl, quinolinyl, iso-quinolinyl, quinazolinyl, quinoxalinyl, or naphthyridinyl-group, and each heteroaryl group is substituted by $R^{10}$, $R^{11}$ and $R^{12}$, while $R^{10}$ denotes a fluorine atom or a difluoromethyl, trifluoromethyl, cyano, methoxy, difluoromethoxy, trifluoromethoxy, dimethylamino, pyrrolidin-1-yl, piperidin-1-yl or morpholin-4-yl group, and $R^{11}$ denotes a cyano group, or $R^1$ denotes a naphthylmethyl group wherein the naphthyl moiety is substituted by $R^{13}$, where $R^{13}$ denotes a difluoromethyl, trifluoromethyl, difluoromethoxy or trifluoromethoxy group, $R^2$ denotes a hydrogen atom or a methyl group, $R^3$ denotes a 2-butyn-1-yl group or a 1-buten-1-yl, 2-buten-1-yl or 3-methyl-2-buten-1-yl group, and n denotes the number 1 or 2, or a tautomer, mixture or salt thereof, with the exception of the compounds:

2-(piperazin-1-yl)-3-(butyn-1-yl)-5-[(pyridin-2-yl)methyl]-3,5-dihydro-imidazo[4,5-d]pyridazin-4-one, 2-(piperazin-1-yl)-3-(butyn-1-yl)-5-[(pyridin-3-yl)methyl]-3,5-dihydro-imidazo[4,5-d]pyridazin-4-one, 2-(piperazin-1-yl)-3-(butyn-1-yl)-5-[(pyridin-4-yl)methyl]-3,5-dihydro-imidazo[4,5-d]pyridazin-4-one, 2-(piperazin-1-yl)-3-(butyn-1-yl)-5-[(2-methoxy-pyridin-3-yl)methyl]-3,5-dihydro-imidazo[4,5-d]pyridazin-4-one, 2-(piperazin-1-yl)-3-(butyn-1-yl)-5-[(2-fluoro-pyridin-3-yl)methyl]-3,5-dihydro-imidazo[4,5-d]pyridazin-4-one, 2-(piperazin-1-yl)-3-(butyn-1-yl)-5-[(2-fluoro-pyridin-4-yl)methyl]-3,5-dihydro-imidazo[4,5-d]pyridazin-4-one, 2-(piperazin-1-yl)-3-(butyn-1-yl)-5-[(6-fluoro-pyridin-2-yl)methyl]-3,5-dihydro-imidazo[4,5-d]pyridazin-4-one and 2-(piperazin-1-yl)-3-(butyn-1-yl)-5-[(isoquinolin-1-yl)methyl]-3,5-dihydro-imidazo[4,5-d]pyridazin-4-one.

3. A compound of formula I according to claim 1, wherein $R^1$ denotes a heteroarylmethyl group, where the term heteroaryl denotes a pyridinyl, pyrimidinyl, benzoxazolyl, 1-methyl-1H-benzotriazolyl, benzo[1,2,5]thiadiazolyl, [1,2,4]-triazolo[4,3-a]pyridinyl, quinolinyl, isoquinolinyl, quinazolinyl, quinoxalinyl, or naphthyridinyl group, and each heteroaryl group is substituted by $R^{10}$, $R^{11}$ and $R^{12}$, where $R^{10}$ denotes a fluorine atom or a cyano, methoxy, dimethylamino, pyrrolidin-1-yl, piperidin-1-yl or morpholin-4-yl group, and $R^{11}$ denotes a cyano group, $R^2$ denotes a hydrogen atom, $R^3$ denotes a 2-butyn-1-yl group and n denotes the number 1 or 2, or a tautomer, mixture or salt thereof, with the exception of the compounds:

2-(piperazin-1-yl)-3-(butyn-1-yl)-5-[(pyridin-2-yl)methyl]-3,5-dihydro-imidazo[4,5-d]pyridazin-4-one, 2-(piperazin-1-yl)-3-(butyn-1-yl)-5-[(pyridin-3-yl)methyl]-3,5-dihydro-imidazo[4,5-d]pyridazin-4-one, 2-(piperazin-1-yl)-3-(butyn-1-yl)-5-[(pyridin-4-yl)methyl]-3,5-dihydro-imidazo[4,5-d]pyridazin-4-one, 2-(piperazin-1-yl)-3-(butyn-1-yl)-5-[(2-methoxy-pyridin-3-yl)methyl]-3,5-dihydro-imidazo[4,5-d]pyridazin-4-one, 2-(piperazin-1-yl)-3-(butyn-1-yl)-5-[(2-fluoro-pyridin-3-yl)methyl]-3,5-dihydro-imidazo[4,5-d]pyridazin-4-one, 2-(piperazin-1-yl)-3-(butyn-1-yl)-5-[(2-fluoro-pyridin-4-yl)methyl]-3,5-dihydro-imidazo[4,5-d]pyridazin-4-one, 2-(piperazin-1-yl)-3-(butyn-1-yl)-5-[(6-fluoro-pyridin-2-yl)methyl]-3,5-dihydro-imidazo[4,5-d]pyridazin-4-one and 2-(piperazin-1-yl)-3-(butyn-1-yl)-5-[(isoquinolin-1-yl)methyl]-3,5-dihydro-imidazo[4,5-d]pyridazin-4-one.

4. A compound of formula I according to claim 1, wherein $R^1$ denotes a methyl group which is substituted by a fluoronaphthyl, bromonaphthyl, methoxynaphthyl, cyanonaphthyl, dicyanonaphthyl, methylpyridinyl, cyanopyridinyl, dimethylpyrimidinyl, phenylpyrimidinyl, methylbenzoxazolyl, 1-methyl-1H-benzo-triazolyl, benzo[1,2,5]thiadiazolyl, [1,2,4]triazolo[4,3-a]pyridinyl, quinolinyl, fluoroquinolinyl, methylquinolinyl, cyanoquinolinyl, methylisoquinolinyl, cyanoiso-quinolinyl, quinazolinyl, methylquinazolinyl, phenylquinazolinyl, (dimethylamino)-quinazolinyl, (morpholin-4-yl)-quinazolinyl, quinoxalinyl, dimethylquinoxalinyl, trimethylquinoxalinyl, or naphthyridinyl group, R² denotes a hydrogen atom,
R³ denotes a 2-butyn-1-yl group,
and n denotes the number 1 or 2,
or a tautomer, mixture or salt thereof.

5. A compound of formula I according to claim 1, wherein
R¹ denotes a methyl group which is substituted by a cyanonaphthyl, methylbenzoxazolyl, 1-methyl-1H-benzotriazolyl, benzo[1,2,5]thiadiazolyl, methylisoquinolinyl, methyl-quinazolinyl or trimethylquinoxalinyl group,
R² denotes a hydrogen atom,
R³ denotes a 2-butyn-1-yl group and
n denotes the number 1 or 2,
or a tautomer or salt thereof.

6. A compound of formula I according to claim 1, wherein
n denotes the number 1,
or a tautomer or salt thereof.

7. A compound of formula I according to claim 1, wherein
n denotes the number 2,
or a tautomer or salt thereof.

8. A compound of formula I according to claim 1 selected from:
(a) 2-(piperazin-1-yl)-3-(2-butyn-1-yl)-5-[(4-methyl-quinazolin-2-yl)methyl]-3,5-dihydro-imidazo[4,5-d]pyridazin-4-one,
(b) 2-([1,4]diazepan-1-yl)-3-(2-butyn-1-yl)-5-[(4-methyl-quinazolin-2-yl)methyl]-3,5-dihydro-imidazo[4,5-d]pyridazin-4-one,
(c) 2-(piperazin-1-yl)-3-(2-butyn-1-yl)-5-[(4-methyl-benzoxazol-2-yl)methyl]-3,5-dihydro-imidazo[4,5-d]pyridazin-4-one,
(d) 2-([1,4]diazepan-1-yl)-3-(2-butyn-1-yl)-5-[(4-methyl-benzoxazol-2-yl)methyl]-3,5-dihydro-imidazo[4,5-d]pyridazin-4-one,
or a tautomer or salt thereof.

9. A compound according to claim 1 in the form of a physiologically acceptable salt with an inorganic or organic acid.

10. A pharmaceutical composition comprising a compound according to claim 1 and one or more inert carriers and/or diluents.

11. A pharmaceutical composition comprising a physiologically acceptable salt according to claim 9 and one or more inert carriers and/or diluents.

12. A method of treating a disease selected from the list consisting of type I and type II diabetes mellitus and obesity in a mammal by administration of a pharmaceutically acceptable amount of a compound according to claim 1.

13. A process for preparing a compound of formula I according to claim 1 comprising the step of reacting a compound of formula (II):

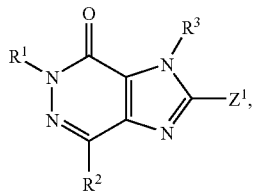

wherein R¹ to R³ are defined in claim 1 and Z¹ denotes a leaving group,
with piperazine or [1,4]diazepan or a salt thereof.

14. A process for preparing a compound of formula I according to claim 1 comprising the step of de-protecting a compound of formula (III):

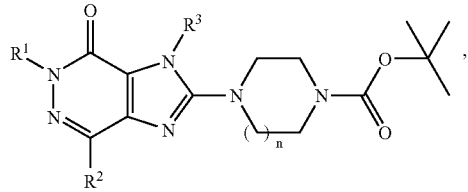

wherein R¹, R² and R³ are defined as in claim 1.

* * * * *